US006380146B1

(12) United States Patent
Breel et al.

(10) Patent No.: US 6,380,146 B1
(45) Date of Patent: Apr. 30, 2002

(54) BLEACHING DETERGENT COMPOSITIONS

(75) Inventors: Greta Johanna Breel; Daniel Convents; Willem Van Liemt; Ton Swarthoff; Robin Stefan Twisker, all of Vlaardingen (NL)

(73) Assignee: Unilever Home & Personal Care USA a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/596,994

(22) Filed: Jun. 20, 2000

(30) Foreign Application Priority Data

Jun. 23, 1999 (EP) ........................................... 99202024

(51) Int. Cl.[7] ........................... C11D 7/42; C11D 3/386; C11D 3/34; C11D 3/30; C12N 9/00

(52) U.S. Cl. ........................ 510/392; 510/392; 510/305; 510/306; 510/311; 510/320; 510/393; 510/374; 510/375; 510/530; 8/137; 8/401

(58) Field of Search ................................ 510/392, 305, 510/306, 311, 320, 393, 374, 375, 530; 8/137, 401

(56) References Cited

U.S. PATENT DOCUMENTS

| | | | | |
|---|---|---|---|---|
| 4,690,895 | A | 9/1987 | Farrell | 435/278 |
| 5,851,233 | A | 12/1998 | Pedersen et al. | 8/102 |
| 5,912,405 | A | 6/1999 | Schneider et al. | 8/111 |
| 5,965,510 | A | 10/1999 | Schneider et al. | 510/397 |

FOREIGN PATENT DOCUMENTS

| | | |
|---|---|---|
| DE | 44 45 088 | 6/1996 |
| EP | 424 398 | 5/1991 |
| EP | 0 453 003 | 10/1991 |
| WO | 91/05839 | 5/1991 |
| WO | 94/12619 | 6/1994 |
| WO | 94/12620 | 6/1994 |
| WO | 94/12621 | 6/1994 |
| WO | 96/12845 | 5/1996 |
| WO | 97/06244 | 2/1997 |
| WO | 97/11217 | 3/1997 |
| WO | 98/51772 | 11/1998 |

OTHER PUBLICATIONS

PCT International Search Report in a PCT application PCT/EP 00/10425. No date.

Derwent Abstract of WO 98/51772—published Nov. 19, 1998.

Derwent Abstract of DE 44 45 088—published Jun. 20, 1996.

PCT International Search Report in a PCT application PCT/EP 00/05232 No date.

PCT International Search Report in a PCT application PCT/EP 00/05233 No date.

European Search Report in a European Application 99 20 2023. No date.

*Primary Examiner*—Lorna M. Douyon
*Assistant Examiner*—Eisa Elhilo
(74) *Attorney, Agent, or Firm*—Rimma Mitelman

(57) ABSTRACT

There is provided a bleaching detergent composition comprising one or more surfactants, a phenol oxidizing enzyme and a compound which acts as enhancer for the phenol oxidizing enzyme, said composition having an Enhancer Index as herein defined of at least 12 and prefereably in the range of 15–50.

13 Claims, No Drawings

BLEACHING DETERGENT COMPOSITIONS

TECHNICAL FIELD

The present invention generally relates to bleaching detergent compositions. More in particular, the invention is concerned with the activation of phenol oxidizing enzymes in a process for bleaching stains on fabrics during washing, without provoking dye damage.

BACKGROUND AND PRIOR ART

Bleaching detergent compositions are well known in the art for removing stains on garments. Modern detergent compositions employ peroxygen compounds such as sodium perborate or sodium percarbonate to oxidize the stains, usually in combination with bleach catalysts such as TAED.

Redox enzymes have also been suggested to bleach stains on fabrics. Redox enzymes are enzymes which catalyze the transfer of electrons from an electron donor to an electron acceptor. In the case of phenol oxidizing enzymes, the electron donor is usually a phenolic compound and the electron acceptor is molecular oxygen or hydrogen peroxide, which is thereby reduced to $H_2O$. Phenol oxidizing enzymes are capable of using a wide variety of different phenolic compounds as electron donors, but they are very specific for molecular oxygen or hydrogen peroxide as the electron acceptor.

Examples of phenol oxidizing enzymes which use molecular oxygen as electron acceptor are laccases (EC 1.10.3.2), bilirubin oxidases (EC 1.3.3.5), mono phenol oxidizing enzymes (EC 1.14.18.1), catechol oxidases (EC 1.10.3.1). Phenol oxidizing enzymes that use hydrogen peroxide as electron acceptor are called peroxidases.

Phenol oxidizing enzymes can be utilised for a wide variety of applications, including the detergent industry, the paper and pulp industry (U.S. Pat. No. 4,690,895), the textile industry and the food industry. In the detergent industry, phenol-oxidizing enzymes have been used for preventing the transfer of dyes in solution from one textile to another during detergent washing, an application commonly referred to as dye transfer inhibition.

For example, the use of peroxidases for bleaching fabrics during washing has been suggested in EP-A-424 398 (Novo Nordisk). WO-A-91/05839 (Novo Nordisk) describes the inhibition of dye transfer during the wash by means of peroxidase or an enzyme exhibiting oxidase activity on phenolic compounds. The compositions are said to bleach any dissolved textile dye so that no dye can redeposit upon the fabric.

It is also known that the activity of phenol oxidizing enzymes may be increased by the addition of certain organic compounds. The use of such activated enzyme systems for various purposes has also been described, for instance for inhibiting dye transfer in a washing process. The above mentioned WO-A-91/05839 (Novo Nordisk) describes that the addition of another oxidisable substrate may enhance the enzyme activity. Examples of such oxidisable substrates or "enhancers" are certain phenolic compounds, e.g. 2,4-dichlorophenol.

In three subsequent patent applications (WO-A-94/12619, WO-A-94/12620 and WO-A-94/12621, all Novo Nordisk) it is disclosed that the action of peroxidase in such anti dye-transfer compositions may be enhanced by the addition of a number of aromatic compounds, of which 2,2'-azo-bis-(3-ethylbenzo-thiazoline-6-sulphonate (ABTS) and Phenothiazine-10-propionate (PTP) appear to be preferred compounds.

The inventors of the present invention have identified an unexpected problem which may occur when phenol oxidising enzymes are used in combination with enhancers compounds to clean soiled fabrics. It was found that enhancers which effectively boost the bleach activity of phenol oxidizing enzyme on stains, may under certain circumstances result in the deterioration of visual appearance of garments. Thus, the enzymatic bleaching of the dyes of coloured fabric could result in undesirable dulling of the garment. This enzymatic bleaching-related dye damage has not been previously discovered in laundry applications and no solutions are at present available. A complicating factor in studying this phenomenon is, that the undesirable dulling of the garment may only become apparent after repeated washing.

Therefore, there is a particular need for bleaching detergent compositions comprising a phenol oxidizing enzyme and an enhancer which specifically bleach stains on fabric, without deteriorating the appearance of coloured garments.

Unexpectedly, it was found that the problem cannot be solved by selecting a particular enhancer or a particular phenol oxidizing enzyme. Rather, the problem appeared to be associated with specific combinations of enhancer and phenol oxidizing enzymes.

We have now surprisingly found that it is possible to obtain detergent compositions which effective bleach stains on fabrics without deteriorating the appearance of coloured garments, i.e. without causing dye damage, if the Enhancer Index (as herein defined) is kept at a value of at least 12 and preferably between 15 and 50.

DEFINITION OF THE INVENTION

According to a first aspect of the invention, there is provided a bleaching detergent composition comprising one or more surfactants, a phenol oxidizing enzyme and a compound which acts as enhancer for the phenol oxidizing enzyme, said composition having an Enhancer Index as herein defined of at least 12.

Preferably, the composition comprises, as an enhancer for the activity of the phenol oxidizing enzyme, one or more compounds having the formula:

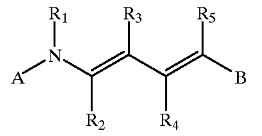

or

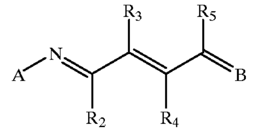

wherein:

A is an optionally substituted electron-withdrawing group, chosen from the group consisting of nitrile, carboxyl, and esters and salts thereof, amides, aldehydes, ketones, sulfoxides, sulfones, or sulphonates, and B is an optionally substituted electron-donating group, chosen from the group consisting of the oxide anion, sulfide anion, oxides, amines, imines, hydroxides, sulfides, ethers, carboxylic acids, and halogen substituents, and $R_1$–$R_5$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, and $R_2$ and $R_5$ together may form an alkylene group or an alkenylene group.

DESCRIPTION OF THE INVENTION

The bleaching detergent composition of the present invention comprise one or more surfactants, a phenol oxidizing enzyme and a compound which acts as enhancer for the phenol oxidizing enzyme, said composition having an Enhancer Index as herein defined of at least 12. The Enhancer Index is defined for the purpose of this invention as the ratio of the bleach effect on tomato stains to the colored monitor P10 ($\Delta E_{tomato\ stain}/\Delta E_{P10\ colored\ monitor}$), and is further illustrated in the Examples. This ratio was found to be a useful property of the composition to determine whether a particular bleaching detergent composition provides selective bleaching, i.e. stain bleaching without colour damage. Preferably, the Enhancer Index is at least 15, and in particular in the range of 15–50.

(a) The Surfactant(s)

The enzymatic bleach compositions according to the invention comprise, as a first constituent, one or more detergent-active compounds (surfactants) which may be chosen from soap and non-soap anionic, cationic, nonionic, amphoteric and zwitterionic detergent-active compounds, and mixtures thereof. Many suitable detergent-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and nonionic compounds. Anionic surfactants are well-known to those skilled in the art. Examples include alkylbenzene sulphonates, particularly linear alkylbenzene sulphonates having an alkyl chain length of $C_8$–$C_{15}$; primary and secondary alkylsulphates, particularly $C_8$–$C_{15}$ primary alkyl sulphates; alkyl ether sulphates; olefin sulphonates; alkyl xylene sulphonates; dialkyl sulpho-succinates; and fatty acid ester sulphonates. Sodium salts are generally preferred.

Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_5$ primary and secondary aliphatic alcohols ethoxylated with an average of from 1 to 10 (and preferably 3 to 7) moles of ethylene oxide per mole of alcohol. Non-ethoxylated nonionic surfactants include alkylpolyglycosides, glycerol monoethers, and polyhydroxyamides (glucamide).

If the detergent composition comprises both nonionic and anionic surfactants, it is preferred that the ratio of nonionic surfactant to anionic surfactant is at least 1 to 3, more preferably at least 1 to 1. The choice of detergent-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The total amount of surfactant present will also depend on the intended end use and may be as high as 60% by weight, for example, in a composition for washing fabrics by hand. In compositions for machine washing of fabrics, an amount of from 5 to 40% by weight is generally appropriate. Detergent compositions suitable for use in most automatic fabric washing machines generally contain anionic non-soap surfactant, or nonionic surfactant, or combinations of the two in any ratio, optionally together with soap.

(b) The Phenol Oxidizing Enzyme

The second element of the bleaching detergent compositions of the invention is the phenol oxidizing enzyme. A phenol oxidizing enzyme is defined for the purpose of the present invention as an enzyme or a system in which an enzyme, by using hydrogen peroxide or molecular oxygen, is capable of oxidising organic compounds containing phenolic groups. Examples of such enzymes are peroxidases and oxidases. Suitable enzymes are disclosed in EP-A-495 835 (Novo Nordisk). For instance, suitable peroxidases may be isolated from and are producible by plants or microorganisms such as bacteria or fungi. Preferred fungi are strains belonging to the class of the Basidiomycetes, in particular Coprinus, or to the class of Hyphomycetes, in particular Arthromyces, especially *Arthromyces ramosus*. Other preferred sources are Hormographiella sp. or Soybean peroxidase. Other relevant peroxidases are haloperoxidases (U.S. Pat. No. 4,397,192) such as chloride peroxidases, bromide peroxidases and iodide peroxidases. Other potential sources of useful peroxidases are listed in B. C. Saunders et al., Peroxidases, London, 1964, pp 41–43.

In the context of this invention, phenol oxidizing enzymes which use oxygen as the oxidant, comprise any laccase comprised by the enzyme classification (EC 1.10.3.2), any catechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.99.1). The phenol oxidizing enzymes are known from microbial and plant origin. The microbial phenol oxidizing enzyme may be derived from bacteria or fungi (including filamentous fungi and yeasts) and suitable examples include a phenol oxidizing enzyme derivable from a strain of Aspergillus, Neurospora, e.g. *N. crasse*, Podospora, Botrytis, Collybia, Fomes, Lentinus, Pleurotus, Trametes, (previously called Polyporus), e.g. *T. villosa* and *T. versicolor*, Rhizoctonia, e.g. *R. solani*, Coprinus, e.g. *C. plicatilis* and *C. cinereus*, Psatyrella, Myceliophthora, e.g. *M. thermophylia*, Schytalidium, Phlebia, e.g. *P. radita* (WO-A-92/01046), Coriolus, e.g. *C. hirsutus* (JP-A-2-238885), Acremonium, e.g *A. murorum*, or Stachybotrys, e.g. *Stachybotrys chartarum* or *Stachybotrys parvispora* (PCT/EP99/02042) (Unilever).

The phenol oxidizing enzyme may furthermore be one which is reproducible by a method comprising cultivating a host cell transformed with a recombinant DNA vector which carried a DNA sequence encoding said phenol oxidizing enzyme as well as DNA sequence encoding functions permitting the expression of the DNA sequence encoding phenol oxidizing enzyme, in a culture medium under conditions permitting the expression of the phenol oxidizing enzyme and the recovery of the phenol oxidizing enzyme from the culture.

Also of interest are synthetic or semi-synthetic derivatives and models of such enzymes, such as those comprising iron or manganese-porphyrin systems, microperoxidases, and iron or manganese-phthalocyanine compounds, e.g. as described in U.S. Pat. No. 4,077,768, WO-A-91/05858 and WO-A-92/16634.

(c) The Source of Hydrogen Peroxide

When a peroxidase is used in the enzymatic bleach compositions according to the invention, it is necessary to include a source of hydrogen peroxide. This may be hydrogen peroxide itself, but more stabilised forms of hydrogen peroxide such as perborate or percarbonate are preferred. Especially preferred is sodium percarbonate.

Alternatively, one may employ an enzymatic hydrogen peroxide-generating system. The enzymatic hydrogen peroxide-generating system may in principle be chosen from the various enzymatic hydrogen peroxide-generating systems which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. In the latter system, superoxide is generated which decomposes to give hydrogen peroxide. Preferably, however, the combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative *Hansenula polymorpha* strain. (see for example EP-A-244 920 (Unilever)).

(d) The Enhancer

As further ingredient, the compositions of the invention comprise an enhancer compound which delivers stain bleaching without provoking dye damage. Preferred enhancers have the following structural formula:

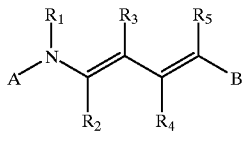

or

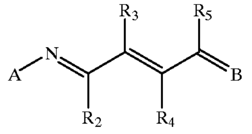

wherein:

A is an optionally substituted electron-withdrawing group, chosen from the group consisting of nitrile, carboxyl, and esters and salts thereof, amides, aldehydes, ketones, sulfoxides, sulfones, or sulphonates, and B is an optionally substituted electron-donating group, chosen from the group consisting of the oxide anion, sulfide anion, oxides, amines, imines, hydroxides, sulfides, ethers, carboxylic acids, and halogen substituents, and $R_1$–$R_5$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, and $R_2$ and $R_5$ together may form an alkylene group or an alkenylene group.

More preferably, the carbamoyl, sulfamoyl and amino groups are further substituted once or twice with hydroxy, $C_1$–$C_6$-alkyl, $C_1$–$C_6$-alkoxy, in which the $C_1$–$C_6$-group may be saturated or unsaturated, branched or unbranched and may be substituted once or twice with halogen, nitroso, hydroxy, formyl, carboxy, and esters and salts thereof, carbamoyl, sulfo, and esters and salts thereof, sulfamoyl; and the phenyl group may be substituted with halogen, nitroso, hydroxy, formyl, carboxy, and esters and salts thereof, carbamoyl, sulfo, and esters and salts hereof, sulfamoyl; and the $C_1$–$C_{20}$ alkyl, $C_1$–$C_8$ alkoxy, carbonyl-$C_1$–$C_6$-alkoxy, and aryl-$C_1$–$C_6$-alkyl groups may be saturated or unsaturated, branched or unbranched, and may be substituted with halogen, hydroxy, nitroso, formyl, carboxy, and esters and salts thereof, carbamoyl, sulfo, and esters and salts thereof, sulfamoyl, nitro, amino, phenyl, aminoalkyl, piperidino, piperazinyl, pyrrolidin-2-yl, $C_1$–$C_6$-alkyl, $C_1$–$C_6$-alkoxy.

Even more preferably, A is a sulfone group —($SO_2$)—R' wherein R' has the same meaning as $R_1$–$R_5$ above. It is especially preferred if R' represents an phenyl group, optionally substituted with 1–5 groups R", whereby R', R" each may independently have the same meaning as $R_1$–$R_5$ above.

Particularly preferred are enhancers having the following formula:

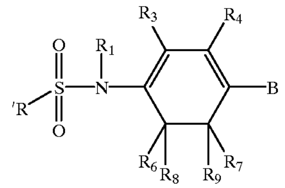

or

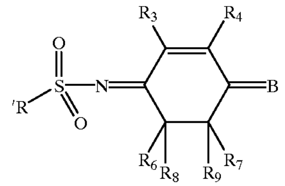

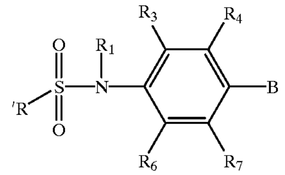

or

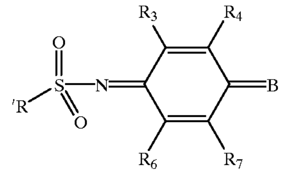

wherein R' represents an phenyl group, optionally substituted with 1–5 groups R", whereby R', R", $R_6$–$R_9$ each may independently have the same meaning as $R_1$–$R_5$ above.

Especially preferred are enhancers wherein B is an hydroxy or oxo group, and one or more of $R_3$, $R_4$, $R_6$–$R_9$ is halogen. Particularly preferred are optionally substituted N-(4-hydroxyphenyl)-benzenesulfonamides.

Examples of these compounds include the following sulfonamides:

N-(2,3,5-tribromo-4-hydroxyphenyl)-Benzenesulfonamide (further referred to as 3BrphenolBSA)

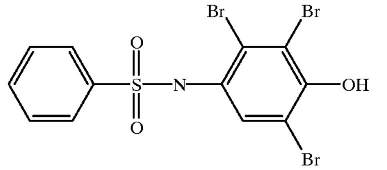

N-(2,3,5-tribromo-4-hydroxyphenyl)-4-Methyl Benzene-sulfonamide (further referred to as 3 BrphenolMeBSA)

N-(2,3,5-tricloro-4-hydroxyphenyl)-Benzenesulfonamide (e) Detergency Builders

The enzymatic bleach compositions of the invention will generally also contain one or more detergency builders. This detergency builder may be any material capable of reducing the level of free calcium ions in the wash liquor and will preferably provide the composition with other beneficial properties such as the generation of an alkaline pH, the suspension of soil removed from the fabric and the suspension of the fabric-softening clay material. The total amount of detergency builder in the compositions will suitably range from 5 to 80%, preferably from 10 to 60% by weight. Inorganic builders that may be present include sodium carbonate, if desired in combination with a crystallisation seed for calcium carbonate, as disclosed in GB-A-1 437 950 (Unilever); crystalline and amorphous aluminosilicates, for example, zeolites as disclosed in GB-A-1 473 201 (Henkel), amorphous aluminosilicates as disclosed in GB-A-1 473 202 (Henkel) and mixed crystalline/amorphous aluminosilicates as disclosed in GB-A-1 470 250 (Procter & Gamble); and layered silicates as disclosed in EP-B-164 (Hacksawed). Inorganic phosphate builders, for example, sodium orthophosphate, pyrophosphate and tripolyphosphate, may also be present, but on environmental grounds those are no longer preferred.

The detergent compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50% by weight. The alkali metal aluminosilicate may be either crystalline or amorphous or mixtures thereof, having the general formula:

$$0.8\text{–}1.5Na_2O.Al_2O_3.0.8\text{–}6SiO_2$$

These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature. Suitable crystalline sodium aluminosilicate ion-exchange detergency builders are described, for example, in GB-A-1 429 143 (Proctor & Gamble). The preferred sodium aluminosilicates of this type are the well-known commercially available zeolites A and X, and mixtures thereof. The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP-A-384 070 (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20. Especially preferred is zeolite MAP having a silicon to aluminium ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyl-iminodiacetates, alkyl- and alkenylmalonates and succinates; and sulphonated fatty acid salts.

Especially preferred organic builders are citrates, suitably used in amounts of from 5 to 30% by weight, preferably from 10 to 25% by weight, and acrylic polymers, more especially acrylic/maleic copolymers, suitably used in amounts of from 0.5 to 15%, preferably from 1 to 10% by weight. Builders, both inorganic and organic, are preferably present in the form of their alkali metal salt, especially their sodium salt.

(f) Additional Bleach Components

Detergent compositions according to the invention may additionally contain a conventional bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate. Especially preferred is sodium percarbonate having a protective coating against destabilisation by moisture. Sodium percarbonate having a protective coating comprising sodium metaborate and sodium silicate is disclosed in GB-A-2 123 044 (Kao). The peroxy bleach compound is suitably present in an amount of from 5 to 35 wt %, preferably from 10 to 25 wt %.

The bleach system may contain apart from the hydrogen peroxide source, as disclosed above, also a peracid-forming bleach activator or precursor to improve bleaching action at low wash temperatures. Preferred bleach precursors are peroxycarboxylic acid precursors, more especially peracetic acid precursors and peroxybenzoic acid precursors; and peroxycarbonic acid precursors. Of special interest or bleach activators such as tetraacetylethylenediamine (TAED) or N,N-phthaloylaminoperoxy caproic acid (PAP). The novel quaternary ammonium and phosphonium bleach precursors disclosed in U.S. Pat. No. 4,751,015 and U.S. Pat. No. 4,818,426 (Lever Brothers Company) and EP-A-402 971 (Unilever) are also of great interest. Alternatively, peroxycarbonic acid precursors, in particular cholyl-4-sulphophenyl carbonate can be used. Also of interest are peroxybenzoic acid precursors, in particular, N,N,N-trimethylammonium toluoyloxy benzene sulphonate; and the cationic bleach precursors disclosed in EP-A-284 292 and EP-A-303 520 (Kao). The bleach precursor is suitably present in an amount of from 1 to 8 wt %, preferably from 2 to 5 wt %.

Alternatively, inorganic peroxyacids like potassium monopersulphate (MPS) may be employed. Alkyl hydroperoxides are another class of peroxy bleaching compounds. Examples of these materials include t-butyl hydroperoxide and cumene hydroperoxide.

Optionally, bleach catalysts can be included. Such compounds are well known in the art and include, for example, manganese-based catalysts as disclosed in U.S. Pat. No. 5,246,621, U.S. Pat. No. 5,244,594, U.S. Pat. No. 5,194,416, U.S. Pat. No. 5,114,606, EP-A-458 397 and EP-A-458 398 EP-A-509 787 or the iron-based catalysts as disclosed in WO-A-95/34628.

A bleach stabilizer (heavy metal sequestrant) may also be present. Suitable bleach stabilizers include ethylenediamine tetraacetate (EDTA) and the polyphosphonates such as Dequest (Trade Mark), EDTMP.

(g) Additional Enzymes

The detergent compositions of the present invention may additionally comprise one or more enzymes, which provide cleaning performance, fabric care and/or sanitation benefits.

Said enzymes include oxidoreductases, transferases, hydrolases, lyases, isomerases and ligases. Suitable members of these enzyme classes are described in Enzyme nomenclature 1992: recommendations of the Nomenclature Committee of the International Union of Biochemistry and Molecular Biology on the nomenclature and classification of enzymes, 1992, ISBN 0-12-227165-3, Academic Press. The most recent information on the nomenclature of enzymes is available on the Internet through the ExPASy WWW server (http://www.expasy.ch/).

Examples of the hydrolases are carboxylic ester hydrolase, thiolester hydrolase, phosphoric monoester hydrolase, and phosphoric diester hydrolase which act on the ester bond; glycosidase which acts on O-glycosyl compounds; glycosylase hydrolysing N-glycosyl compounds; thioether hydrolase which acts on the ether bond; and exopeptidases and endopeptidases which act on the peptide bond. Preferable among them are carboxylic ester hydrolase, glycosidase and exo- and endopeptidases. Specific examples of suitable hydrolases include (1) exopeptidases such as aminopeptidase and carboxypeptidase A and B and endopeptidases such as pepsin, pepsin B, chymosin, trypsin, chymotrypsin, elastase, enteropeptidase, cathepsin B, papain, chymopapain, ficain, thrombin, plasmin, renin, subtilisin, aspergillopepsin, collagenase, clostripain, kallikrein, gastricsin, cathepsin D, bromelain, chymotrypsin C, urokinase, cucumisin, oryzin, proteinase K, thermomycolin, thermitase, lactocepin, thermolysin, bacillolysin. Preferred among them is subtilisin; (2) glycosidases such as α-amylase, β-amylase, glucoamylase, isoamylase, cellulase, endo-1,3(4)-β-glucanase (β-glucanase), xylanase, dextranase, polygalacturonase (pectinase), lysozyme, invertase, hyaluronidase, pullulanase, neopullulanase, chitinase, arabinosidase, exocellobiohydrolase, hexosaminidase, mycodextranase, endo-1,4-β-mannanase (hemicellulase), xyloglucanase, endo-β-galactosidase (keratanase), mannanase and other saccharide gum degrading enzymes as described in WO-A-99/09127. Preferred among them are a-amylase and cellulase; (3) carboxylic ester hydrolase including carboxylesterase, lipase, phospholipase, pectinesterase, cholesterol esterase, chlorophyllase, tannase and wax-ester hydrolase. Preferred among them is lipase.

Examples of transferases and ligases are glutathione S-transferase and acid-thiol ligase as described in WO-A-98/59028 and xyloglycan endotransglycosylase as described in WO-A-98/38288.

Examples of lyases are hyaluronate lyase, pectate lyase, chondroitinase, pectin lyase, alginase II. Especially preferred is pectolyase, which is a mixture of pectinase and pectin lyase.

A process for enhancing the efficacy of the bleaching action of oxidoreductases is by targeting them to stains by using antibodies or antibody fragments is described in WO-A-98/56885. Antibodies can also be added to control enzyme activity as described in WO-A-98/06812.

A preferred combination is a detergent composition comprising of a mixture of conventional detergent enzymes such as protease, amylase, lipase, cutinase and/or cellulase together with one or more plant cell wall degrading enzymes.

Endopeptidases (proteolytic enzymes or proteases) of various qualities and origins and having activity in various pH ranges of from 4–12 are available and can be used in the instant invention. Examples of suitable proteolytic enzymes are the subtilisins, which can be obtained from particular strains of *B. subtilis, B. lentus, B. amyloliquefaciens* and *B. licheniformis*, such as the commercially available subtilisins Savinase™, Alcalase™, Relase™, Kannase™ and Everlase™ as supplied by Novo Industri A/S, Copenhagen, Denmark or Purafect™, PurafectOxP™ and Properase™ as supplied by Genencor International. Chemically or genetically modified variants of these enzymes are included such as described in WO-A-99/02632 pages 12 to 16 and in WO-A-99/20727 and also variants with reduced allergenicity as described in WO-A-99/00489 and WO-A-99/49056.

Suitable lipases include those of bacterial or fungal origin as described in WO-A-99/11770 pages 33, 34, such as the commercially available Lipolase™, Lipolase Ultra™, LipoPrime™, from Novo Nordisk, or Lipomax™ from Genencor. Chemically or genetically modified variants of these enzymes are included.

Suitable amylases include those of bacterial or fungal origin. Chemically or genetically modified variants of these enzymes are included as described in WO-A-99/02632 pages 18, 19. Commercial cellulase are sold under the tradename Purastar™, Purastar OxAm™ (formerly Purafact Ox Am™) by Genencor; Termamyl™, Fungamyl™ and Duramyl™, all available from Novo Nordisk A/S.

Suitable cellulases include those of bacterial or fungal origin. Chemically or genetically modified variants of these enzymes are included as described in WO-A-99/02632 page 17. Particularly useful cellulases are the endoglucanases such as the EGIII from *Trichoderma longibrachiatum* as described in WO-A-94/21801 and the E5 from *Thermomonospora fusca* as described in WO-A-97/20025. Endoglucanases may consist of a catalytic domain and a cellulose binding domain or a catalytic domain only. Preferred cellulolytic enzymes are sold under the tradename Carezyme™, Celluzyme™ and Endolase™ by Novo Nordisk A/S; Puradax™ is sold by Genencor and KAC™ is sold by Kao corporation, Japan.

Detergent enzymes are usually incorporated in an amount of 0.00001% to 2%, and more preferably 0.001% to 0.5%, and even more preferably 0.01% to 0.2% in terms of pure enzyme protein by weight of the composition. Detergent enzymes are commonly employed in the form of granules made of crude enzyme alone or in combination with other components in the detergent composition. Granules of crude enzyme are used in such an amount that the pure enzyme is 0.001 to 50 weight percent in the granules. The granules are used in an amount of 0.002 to 20 and preferably 0.1 to 3 weight percent. Granular forms of detergent enzymes are known as Enzoguard™ granules, prills, marumes or T-granules. Granules can be formulated so as to contain an enzyme protecting agent (e.g. oxidation scavengers) and/or a dissolution retardant material. Other suitable forms of enzymes are liquid forms such as the "L" type liquids from Novo Nordisk, slurries of enzymes in nonionic surfactants such as the "SL" type sold by Novo Nordisk and microencapsulated enzymes marketed by Novo Nordisk under the tradename "LDP" and "CC".

The enzymes can be added as separate single ingredients (prills, granulates, stabilised liquids, etc. containing one enzyme) or as mixtures of two or more enzymes (e.g. cogranulates). Enzymes in liquid detergents can be stabilised by various techniques as for example disclosed in U.S. Pat. Nos. 4,261,868 and 4,318,818.

The detergent compositions of the present invention may additionally comprise one or more biologically active peptides such as swollen in proteins, expansins, bacteriocins and peptides capable of binding to stains.

Detergency enzymes are commonly employed in granular form in amounts of from about 0.1 to about 3.0 wt %.

(h) Other Ingredients

The compositions of the invention may also contain alkali metal, preferably sodium, carbonate, in order to increase detergency and ease processing. Sodium carbonate may suitably be present in amounts ranging from 1 to 60 wt %, preferably from 2 to 40 wt.

Powder flow may be improved by the incorporation of a small amount of a powder structurant, for example, a fatty acid (or fatty acid soap), a sugar, an acrylate or acrylate/maleate polymer, or sodium silicate. One preferred powder structurant is fatty acid soap, suitably present in an amount of from 1 to 5 wt %.

The detergent compositions according to the present invention may also comprise from 0.001% to 10%, more preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash. Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Soil release agents useful in compositions of the present invention are conventionally copolymers or terpolymers of terephthalic acid with ethylene glycol and/or propylene glycol units in various arrangements. Examples of such polymers are disclosed in U.S. Pat. No. 4,116,885, U.S. Pat. No. 4,711,730 and EP-A-272 033.

Other materials that may be present in detergent compositions of the invention include sodium silicate; antiredeposition agents such as cellulosic polymers; inorganic salts such as sodium sulphate, lather control agents or lather boosters as appropriate, enzyme stabilizers, corrosion inhibitors, dyes, coloured speckles, perfumes, suds depressants, germicides, anti-tarnishing agents, opacifiers, optical brighteners, foam controllers, and fabric softening compounds. This list is not intended to be exhaustive.

(i) Applications

The process and the bleach composition of the present invention may in principle be applied in all situations where phenol oxidizing enzymes are now used or have been suggested for use, such as in fabric washing, pulp bleaching in the paper industry and waste water treatment. The invention is of particular use to formulate detergent compositions that are capable of bleaching stains on fabrics during washing, but also to formulate enzymatic anti dye-transfer compositions. The enzymatic bleach compositions and the detergent compositions of the invention may take any suitable physical form, such as a powder, an aqueous or non-aqueous liquid (which may be stuctured or isotropic), a paste, a gel or a tablet. However, granular detergents (powders) are preferred.

The enzymatic bleach compositions of the invention comprise about 0.001 to 50 mg of active enzyme per gram of detergent composition. Preferably, they comprise 0.001 to 5 mg of active enzyme protein per gram of detergent composition, more preferably 0.005 to 1.0 mg per gram. The phenol oxidizing enzymes used in the present invention can usefully be added to detergent compositions in any suitable form, i.e. the form of a granular composition, a liquid or a slurry of the enzyme, with carrier material (e.g. as in EPA-258 068 and the Savinase™ and Lipolase™ products of Novo Nordisk), or a coating. A good way of adding the enzyme to a liquid detergent product is in the form of a slurry containing 0.5 to 50 % by weight of the enzyme in a ethoxylated alcohol nonionic surfactant, such as described in EP-A-450 702 (Unilever).

If desired, a slow-release coating may be applied to the granulate of the phenol oxidizing enzyme. By means of such coatings, it is possible to achieve the controlled release of the enzyme when the granulate is introduced in the washing liquor. Preferred slow-release materials are compounds that are substantially insoluble in water. Examples of such materials include long-chain fatty acid mono, di-, triesters of glycerol, ethoxylated fatty alcohols, latexes, waxes, tallow, hydrogenation tallow, partially hydrolyzed tallow, hydrocarbons having a melting point in the range of 50–80° C.

Detergent compositions of the invention may be prepared by any suitable method. Particulate detergent compositions are suitably prepared by spray-drying a slurry of compatible heat-insensitive ingredients, and then spraying on or post-dosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l. Such powders may be prepared either by post-tower densification of spray-dried powder, or by wholly non-tower methods such as dry mixing and granulation; in both cases a high-speed mixer/granulator may advantageously be used. Processes using high-speed mixer/granulators for preparing high-bulk density detergent powders are disclosed, for example, in EP-A-340 013, EP-A-367 339, EP-A-390 251 and EP-A-420 317 (Unilever).

The invention will now be further illustrated in the following, non-limiting Examples.

EXAMPLE 1

Bleaching of Tomato Stains.

The potential of the various enhancer to boost the bleach performance of phenol oxidizing enzyme was assessed by washing cotton swatches soiled with tomato stains. Two different bleach monitors were used:

Tomato extract material was prepared by acetone extraction of the chromophores from concentrated tomato paste. For the preparation of the stains, the colored acetone solution was applied to cotton swatches Oily tomato stains were prepared by applying heated concentrated tomato paste, to which 5 wt % Soya oil was added, to cotton swatches.

The experiments were performed in small 80 ml containers, to which 15 ml of wash solution were added (indicated in tables). The pH of the wash solution was set to pH 9. Purified phenol oxidizing enzyme from *Acremonium murorum* was added to the wash solution at 20 mg/l. The enzyme from *Acremonium murorum* is described in WO-A-00/05349 (Unilever). The enhancers were all dosed at 250 μM. The wash solution was 50 mM Tris buffer.

The swatches were washed during 30 minutes, at 30° C. After the wash, the swatches were tumble-dried and the reflectance spectra were measured using a Minolta spectrometer. The color differences between the swatch before and after the wash data were expressed in the CIELAB L*a*b* color space. In this color space, L* indicates lightness and a* and b* are the chromaticity coordinates. Color differences between two swatches are expressed as ΔE, which is calculated from the following equation:

$$\Delta E=\sqrt{\Delta L^2+\Delta a^2+\Delta b^2}$$

As can be seen from the ΔE values, the bleaching of the tomato stain is improved in the presence of the phenol oxidizing enzyme/enhancer system.

TABLE 1

Stain bleach performance of the phenol oxidizing enzyme/enhancer system on tomato stains in the presence of different enhancers. The detergent formulation shown in the table below was used as wash solution (at 2 g/l)

| | Stain Monitor | | | |
|---|---|---|---|---|
| | Tomato Extract | | Oily Tomato Stain | |
| Enhancer | Without enzyme | With enzyme | Without enzyme | With enzyme |
| ABTS | 11.12 | 37.56 | 8.67 | 27.53 |
| PTP | 12.00 | 33.66 | 8.54 | 9.41 |
| 3BrphenolBSA | 12.99 | 26.87 | 6.89 | 10.95 |
| 3Brphenol3MeBSA | 12.86 | 27.57 | 6.87 | 11.71 |

The detergent formulation used above is given below. The amounts are given in weight%.

| | |
|---|---|
| Linear Alkylbenzene Sulphonate (LAS) | 24.0 |
| Sodium tripolyphosphate | 14.5 |
| Soda ash | 17.5 |
| Sodium silicate | 8.0 |
| SCMC | 0.37 |
| Blue pigment | 0.02 |
| Moisture/salts | ad 100 |

TABLE 2

Stain bleach performance of the phenol oxidizing enzyme/enhancer system on tomato stains in the presence of different enhancers. A 50 mM Tris buffer solution was used as the wash solution.

| | Stain Monitor | | | |
|---|---|---|---|---|
| | Tomato Extract | | Oily Tomato Stain | |
| Enhancer | Without enzyme | With enzyme | Without enzyme | With enzyme |
| ABTS | 9.4 | 35.7 | 3.50 | 32.39 |
| PTP | 10.71 | 34.71 | 4.08 | 6.64 |
| 3BrphenolBSA | 10.33 | 19.97 | 4.18 | 5.62 |
| 3Brphenol3MeBSA | 10.86 | 19.59 | 1.56 | 6.21 |

EXAMPLE 2

Dye Damage of the Phenol Oxidizing Enzyme/Enhancer System.

A number of colored swatches were washed to assess the degree to which the enzymatic bleach system provokes dye damage. Each swatch was subjected to 5 consecutive washes in a detergent formulation. The experiments were performed in small 80 ml containers, to which 15 ml of wash solution was added (indicated in tables). The closed containers were agitated by putting them in a washing machine. The machine was run for 1 hour with the water heated to 40° C. The pH of the wash solution was set to pH 9. The phenol oxidizing enzyme from *Acremonium murorum* (see above) was added to the wash solution at 20 mg/l. The enhancers were all dosed at 250 μM. After the wash, the color difference between the swatches before and after the indicated number of washes was measured using the same methodology as in example 1. The resulting color differences (ΔE) are given in the tables below.

TABLE 3

Color difference between the original P10 swatch and the swatch after the indicated number of washes in the presence of the different enhancers. The washes were performed in the detergent formulation shown above.

| Enhancer | 1st wash | 2nd wash | 3rd wash | 4th wash | 5th wash |
|---|---|---|---|---|---|
| None | 0.63 | 0.7 | 0.38 | 0.55 | 0.64 |
| ABTS | 1.61 | 1.51 | 3.29 | 4.99 | 6.52 |
| PTP | 0.51 | 0.78 | 1.79 | 2.63 | 3.25 |
| 3BrphenolBSA | 1.69 | 1.17 | 1.20 | 1.55 | 1.77 |
| 3Brphenol3MeBSA | 0.93 | 0.98 | 1.10 | 1.62 | 1.86 |

TABLE 4

Color difference between a number of dyed swatches (OO6, PO8, P10 and OO2) in their original state and the swatches after 3 washes in the presence of the different enhancers. The washes were performed in Tris buffer pH 8.

| | Dyed Monitor | | | |
|---|---|---|---|---|
| Enhancer | OO6 | PO8 | P10 | OO2 |
| None | 3.21 | 0.58 | 0.64 | 1.63 |
| ABTS | 19.70 | 24.02 | 12.18 | 3.47 |
| PTP | 15.64 | 12.57 | 9.66 | 6.34 |
| 3BrphenolBSA | 4.45 | 1.45 | 1.00 | 0.47 |
| 3Brphenol3MeBSA | 4.59 | 1.52 | 0.96 | 0.41 |

EXAMPLE 3

In order to express the potential of the various enhancers to provoke stain bleaching in the absence of dye damage, the ratio of bleach effect on the tomato stains to the colored monitor P10 was calculated ($\Delta E_{tomato\ stain}/\Delta E_{P10\ colored\ monitor}$). This ratio, when tomato extract is used as the stain, is referred to as the 'Ehancer Index'. The results of the washes, done in the detergent formulation shown above and a 50 mM Tris buffer solution were taken from example 1 and example 2.

TABLE 5

Ratio of the tomato stain bleach over dye damage on P10 in a detergent formulation (see above).

| Enhancer | Ratio Bleach on Stain Monitor/ Dye Damage: Tomato Extract | Ratio Bleach on Stain Monitor/ Dye Damage: Oily Tomato Stain |
|---|---|---|
| ABTS | 5.76 | 4.22 |
| PTP | 10.35 | 2.89 |
| 3BrphenolBSA | 15.18 | 6.18 |
| 3Brphenol3MeBSA | 14.82 | 6.29 |

TABLE 6

Ratio of the tomato stain bleach over dye damage on P10 in a 50 mM Tris buffer solution.

| Enhancer | Ratio Bleach on Stain Monitor/ Dye Damage: Tomato Extract | Ratio Bleach on Stain Monitor/ Dye Damage: Oily Tomato Stain |
|---|---|---|
| ABTS | 2.93 | 2.66 |
| PTP | 3.59 | 0.69 |
| 3BrphenolBSA | 19.97 | 5.62 |
| 3Brphenol3MeBSA | 20.40 | 6.46 |

The ratios clearly indicate that these detergent compositions have a superior stain bleach selectivity. In other words, these compositions deliver stain bleaching without damaging colored garments.

What is claimed is:

1. Bleaching detergent composition comprising one or more surfactants, a phenol oxidizing enzyme and a compound which acts as enhancer for the phenol oxidizing enzyme, said composition having an Enhancer Index of at least 12, wherein the enhancer has a formula:

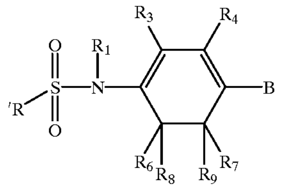

or

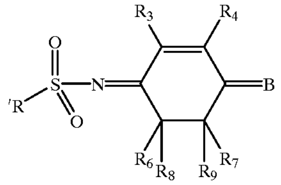

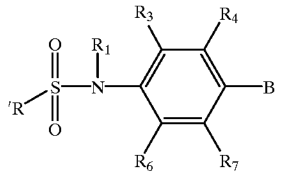

or

-continued

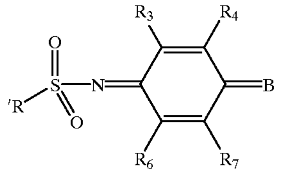

wherein R' represents an phenyl group, optionally substituted with 1–5 groups R", whereby R", $R_1$, $R_3$, $R_4$, $R_6$–$R_9$ each may independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, B is an optionally substituted electron-donating group, chosen from the group consisting of the oxide anion, sulfide anion, oxides, amines, imines, hydroxides, sulfides, ethers, carboxylic acids.

2. Composition according to claim 1, having an Enhancer Index in the range of 15–50.

3. Composition according to claim 1, wherein B is an hydroxy or oxo group, and one or more of $R_3$, $R_4$, $R_6$–$R_9$ is halogen.

4. Composition according to claim 1, wherein the enhancer is an optionally subsituted N-(4-hydroxyphenyl)-benzenesulfonamide.

5. Composition according to claim 1, wherein the enhancer is N-(2,3,5-tribromo4-hydroxyphenyl)-benzenesulfonamide, N-(2,3,5-tribromo4-hydroxyphenyl) 4methyl benzene-sulfonamide, or N-(2,3,5-trichloro4-hydroxyphenyl)benzenesulfonamide.

6. Composition according to claim 1, comprising (a) an enzyme exhibiting peroxidase activity and a source of hydrogen peroxide.

7. Composition according to claim 6, wherein the source of hydrogen peroxide is an alkali metal percarbonate, preferably sodium percarbonate.

8. Composition according to claim 6, wherein the amount of hydrogen peroxide is from 0.001 to 10 mM.

9. Composition according to claim 1, further comprising a proteolytic enzyme.

10. Composition according to claim 1, further comprising a subtilisin protease.

11. Composition according to claim 1, in the form of an granular detergent composition.

12. Process for removing coloured stains from fabrics in a washing process comprising contacting the stained fabric, in an aqueous medium, with a composition according to claim 1.

13. Composition according to claim 6, wherein the amount of hydrogen peroxide is from 0.005 to 1 mM.

* * * * *